US012784921B2

(12) United States Patent
Olatunji

(10) Patent No.: US 12,784,921 B2
(45) Date of Patent: Nov. 3, 2026

(54) SYSTEM TO GENERATE STRUCTURED MEDICAL OPERATION AND PROCEDURE NOTES USING VOICE NARRATION DURING SURGERY

(71) Applicant: Intron Inc, Dover, DE (US)

(72) Inventor: Oloruntobiloba Olatunji, Menlo Park, CA (US)

(73) Assignee: Intron Inc.

(*) Notice: Subject to any disclaimer, the term of this patent is extended or adjusted under 35 U.S.C. 154(b) by 0 days.

(21) Appl. No.: 19/058,299

(22) Filed: Feb. 20, 2025

(65) Prior Publication Data

US 2026/0245747 A1 Aug. 20, 2026

(51) Int. Cl.
*G16H 80/00* (2018.01)
*G16H 40/40* (2018.01)

(52) U.S. Cl.
CPC ............. *G16H 80/00* (2018.01); *G16H 40/40* (2018.01)

(58) Field of Classification Search
None
See application file for complete search history.

(56) References Cited

U.S. PATENT DOCUMENTS

2022/0115019 A1* 4/2022 Bradley ................ G10L 15/063
2025/0166617 A1* 5/2025 Grantcharov ........... G10L 15/16
2025/0336393 A1* 10/2025 Zhou ...................... G16H 15/00

FOREIGN PATENT DOCUMENTS

WO WO-2025078999 A1 * 4/2025 ............ G06F 40/56

OTHER PUBLICATIONS

Bain, Max & Huh, Jaesung & Han, Tengda & Zisserman, Andrew. (2023). WhisperX: Time-Accurate Speech Transcription of Long-Form Audio. 10.48550/arXiv.2303.00747. (Year: 2023).*
Ahamed S, Weiler G, Boden K, et al. Deep neural network driven speech classification for relevance detection in automatic medical documentation. In: Public Health and Informatics: Proceedings of MIE 2021. SAGE Publications; 2021:63-67. doi:10.3233/SHTI210121 (Year: 2021).*

* cited by examiner

*Primary Examiner* — Devin C Hein
(74) *Attorney, Agent, or Firm* — The Rapacke Law Group, P.A.

(57) ABSTRACT

A computer-implemented method for generating structured surgical or medical operation and procedure notes using voice narration during surgery may include recording, via a wearable computing device including at least one microphone, real-time audio; communicating the real-time audio to a local, on-premises, private, or cloud-based server or processor; sectioning intelligently the real-time audio to detect and classify relevant audio segments; transcribing the sectioned real-time audio data in parallel via two or more instances of voice-to-text or speech recognition models; combining transcribed sections into a single transcript; generating, via a post-processing step, heuristics, or large language model, structured operation notes based on the single transcript or sections; and altering, via post-processing steps, heuristics, or the large language model, the single transcript, or transcribed sections into the structured operation notes.

17 Claims, 6 Drawing Sheets

SYSTEM TO GENERATE STRUCTURED MEDICAL OPERATION AND PROCEDURE NOTES USING VOICE NARRATION DURING SURGERY

TECHNICAL FIELD

The embodiments generally relate to the technical field of real-time audio-based surgical documentation, specifically utilizing voice narration during medical procedures to generate structured operation and procedure notes.

BACKGROUND

Conventional system for the generation of structured medical operation and procedure notes is a critical aspect of surgical documentation, ensuring accuracy in patient records, compliance with legal and regulatory standards, and effective communication among healthcare providers. Traditional post-operative documentation methods require surgeons and medical professionals to manually draft notes after a procedure, often relying on recollection after consecutive surgeries. This process introduces inefficiencies due to the cognitive load on clinicians, potential omissions of critical details, and time delays in finalizing reports. Existing solutions, such as template-based documentation and voice dictation software, partially alleviate this burden but still require recollection, dedicated time post-surgery, and necessitate manual intervention for structuring and verification. Additionally, although Surgeons typically discuss the ongoing procedure with surgical teams, assistants, and trainees, the practice of intra-operative audio narration with voice recording by Surgeons is not commonplace.

Current speech recognition and transcription systems are generically designed for clinicians, with no intra-operative surgical workflow integration. They are not designed to collect and process extended real-time surgical audio streams effectively. Due to the long duration of medical procedures, unprocessed voice data accumulates, resulting in high latency and computational inefficiencies. Additionally, speech-to-text conversion models frequently misinterpret domain-specific medical terminology, procedural sequences, and instrument names, leading to transcription errors. Many existing medical documentation systems lack intelligent segmentation of intra-operative surgical audio recording, parallel processing of such audio streams, or structured output generation, requiring extensive post-processing to ensure medical accuracy. Furthermore, conventional surgical transcription tools do not dynamically structure output into standardized procedural formats, limiting their utility for surgical documentation.

Another limitation of existing systems is their inability to operate efficiently in sterile surgical environments. Hands-free operation and real-time audio processing are essential in operating rooms where direct interaction with computing devices is impractical. The lack of seamless integration between real-time audio capture, intelligent segmentation, medical language models, and structured documentation generation results in fragmented workflows and increased administrative workload. An optimized system must intelligently record, process, and structure surgical narration with minimal latency while ensuring domain-specific accuracy, compliance, and usability in medical settings.

SUMMARY

This summary is provided to introduce a variety of concepts in a simplified form that is further disclosed in the detailed description of the embodiments. This summary is not intended to identify key or essential inventive concepts of the claimed subject matter, nor is it intended to determine the scope of the claimed subject matter.

A system is disclosed for generating organized medical notes during surgery by capturing the surgeon's voice in real time using a wearable device including a sterile wireless microphone or headset. The system then transmits the recorded audio to a local or cloud-based computer for processing. The system breaks the audio into smaller, meaningful sections before transcribing them using multiple voice-to-text programs simultaneously. After transcription, the system merges the sections into a single, complete document. Advanced algorithms or AI then process the document, structuring it into clear and organized post-operative notes. The system then refines the notes using AI or additional processing to enhance clarity and accuracy.

The disclosed system processes segmented audio in parallel using multiple speech recognition models optimized for medical terminology. Post-processing modules apply linguistic corrections, semantic validation, and formatting based on predefined surgical documentation standards, ensuring accurate and structured output.

Real-time synchronization between the wearable device and the processing server ensures low-latency data transfer and processing. Machine learning-based filtering removes background noise and non-procedural dialogue, enhancing transcription accuracy and efficiency.

Authorized users, including surgeons and medical staff, can review, edit, and validate the generated documentation. The system integrates with hospital information systems (HIS) and electronic health records (EHR) and supports augmented reality (AR) and virtual reality (VR) interfaces for hands-free interaction.

In emergency scenarios, the system prioritizes critical sections of the transcript for rapid documentation. Using distributed computing and AI-driven structured documentation, the system optimizes workflow efficiency, reduces cognitive load on medical professionals, and ensures comprehensive and accurate surgical records.

Other illustrative variations within the scope of the invention will become apparent from the detailed description provided hereinafter. The detailed description and enumerated variations, while disclosing optional variations, are intended for purposes of illustration only and are not intended to limit the scope of the invention.

BRIEF DESCRIPTION OF THE DRAWINGS

A more complete understanding of the embodiments, and the attendant advantages and features thereof, will be more readily understood by references to the following detailed description when considered in conjunction with the accompanying drawings wherein.

DETAILED DESCRIPTION

Figure 1:
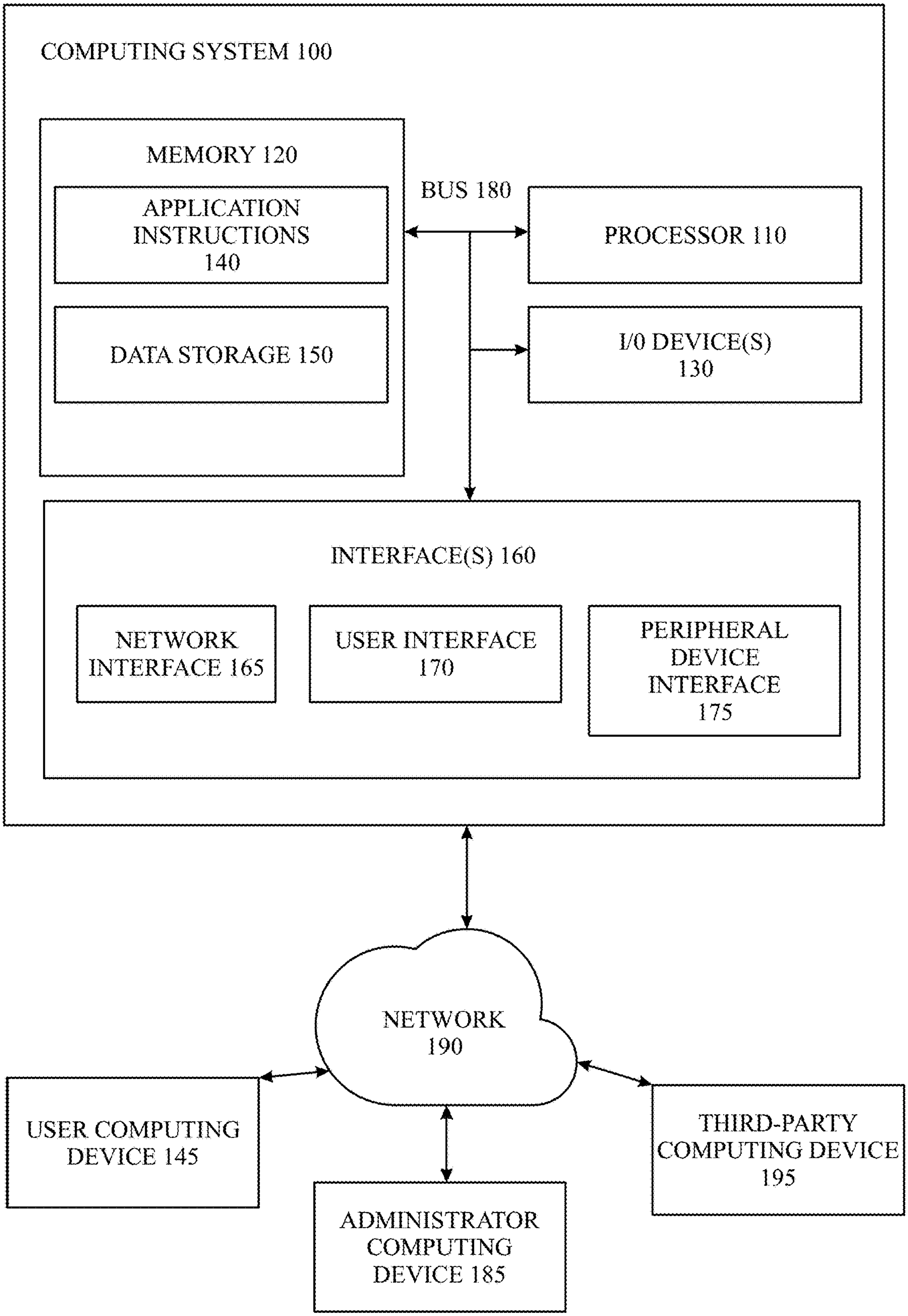
FIG. 1 illustrates a system architecture diagram, according to some embodiments.

The specific details of the single embodiment or variety of embodiments described herein are set forth in this application. Any specific details of the embodiments described herein are used for demonstration purposes only, and no unnecessary limitation(s) or inference(s) are to be understood or imputed therefrom.

Before describing exemplary embodiments in detail, it is noted that the embodiments reside primarily in combinations of components related to devices and systems. Accordingly, the device components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

The system comprises a wearable computing device (e.g., a headset, lapel microphone, or other sterile-compatible audio input device) capable of real-time audio recording. The device includes at least one microphone designed to capture high-fidelity surgical narration while minimizing background noise. This microphone is connected to a wireless transmission module (e.g., Bluetooth, Wi-Fi, or other communication protocols) that streams real-time audio to a computing device (e.g., a smartphone, tablet, laptop, or processing server for intelligent segmentation and transcription.

The computing device can be connected to or deployed in a cloud-based environment, an on-premises private server, or a local computing device within the operating room. The computing device receives the incoming audio stream and transmits it to the server. The server subsequently processes it using an intelligent segmentation module that divides the real-time narration into discrete segments based on natural language processing (NLP), procedural context, and acoustic analysis. This segmentation detects and removes irrelevant audio segments such as silence and background noise, and background conversations, and ensures that each segment of the audio corresponds to distinct phases of the procedure, such as preoperative preparation, incision, closure, and postoperative care.

Once segmented, the system employs a parallel transcription module utilizing multiple speech-to-text models. These models may include deep learning-based speech recognition engines, such as transformer-based Automatic Speech Recognition (ASR) models, that analyze the segmented audio. The system identifies phonemes, linguistic structures, and procedural terminology, ensuring high accuracy in transcription. The voice recognition module is pre-trained on extensive medical datasets to recognize surgical terminology, abbreviations, and procedural steps. In some embodiments, the voice recognition module is accent-aware by being trained on a diverse dataset of speech from various accents, which helps the system learn to recognize and adapt to different pronunciation patterns.

A post-processing module refines the transcription by applying heuristic-based filtering, contextual reorganization, and medical domain-specific corrections. The post-processing module uses semantic analysis to detect primary procedural components, syntactic alignment models to ensure proper sentence structure, and noise filtering algorithms to remove irrelevant audio artifacts. Additionally, an auto-correction module cross-references detected terms against a medical knowledge base to validate medical terminology and ensure coherence.

The processed transcript is then passed to the structured documentation generation module, which organizes the information into a structured format aligned with standard surgical documentation protocols. The structured notes may be generated in standardized formats or custom institutional templates. The system allows customization based on hospital-specific procedural or post-operative note requirements, enabling automated compliance with regulatory standards.

The system includes a real-time synchronization protocol that continuously updates the structured notes as the narration progresses. The structured notes are displayed on a user interface, such as a tablet, desktop, mobile application, or augmented reality (AR) and virtual reality (VR) headset, allowing real-time review and editing. The interface supports keyboard inputs, touch gestures, and voice commands for hands-free interaction and post-procedure modifications.

A context-aware filtering mechanism is employed to detect and eliminate irrelevant transcript segments. This mechanism incorporates machine learning-based speech classification, which distinguishes between procedural narration, intraoperative discussions, irrelevant chatter, and background conversations. This ensures that only relevant procedural details are transcribed into the structured notes, reducing unnecessary data storage and enhancing clarity.

The system further integrates with electronic health records (EHR) and hospital information systems (HIS) via one or more interfaces, such as an application programming interface. This enables automated documentation uploads, reducing manual data entry and administrative workload for medical professionals.

In addition to structured documentation, the system supports metadata tagging, associating timestamps, procedural steps, administrative billing codes, and surgical instruments used during the procedure. These metadata tags enhance searchability, enable procedural audits, and facilitate training applications where recorded surgeries can be used for educational purposes.

To support emergency and high-priority use cases, the system implements a low-latency emergency mode, where key sections of the procedure are prioritized for immediate transcription. This allows for quick summary generation for trauma cases, enabling medical staff to access critical procedural notes in real time.

A role-based access control system ensures that only authorized personnel can access or modify the generated notes. Access control is managed via secure authentication protocols, such as multi-factor authentication (MFA) and biometric verification. This enhances security while maintaining compliance with HIPAA (Health Insurance Portability and Accountability Act) and GDPR (General Data Protection Regulation) requirements.

By integrating wearable audio capture, real-time transcription, AI-driven post-processing, structured documentation generation, and seamless hospital system integration, this system significantly reduces the cognitive load on surgeons and medical professionals, enhances recall and documentation accuracy, quality, and improves overall workflow efficiency.

Various implementations of the invention involve the technical field of real-time audio-based surgical documentation including recording, via a wearable computing device including at least one microphone, real-time audio; communicating the real-time audio to a local, on-premises, private, or cloud-based server or processor via a computing device such as a laptop or desktop computer, smartphone or tablet as needed; sectioning intelligently the real-time audio; transcribing the sectioned real-time audio data in parallel via two or more instances of voice-to-text or speech recognition models; combining transcribed sections into a single transcript; generating, via a post-processing step comprising heuristics or a large language model, structured operation notes based on the single transcript or sections; and altering, via post-processing steps, heuristics, or the large language model, the single transcript, or transcribed sections into the structured operation notes and are therefore necessarily rooted in computer technology. For example, the aforementioned steps are inherently computer-based and cannot be performed in the human mind and they amount to more than merely implementing the generic computer as a tool to gather, analyze, and output data. Additionally, the steps of the present invention would be impossible to accomplish on pen and paper due to the volume of data being communicated and received over a network in real-time. In particular, the speed at which the steps of the present invention occur to effectuate the disclosed method, system, or product would involve large-scale, continuous wireless communication of such data. That is, the steps of the present method, system, or product are impossible to accomplish on pen and paper, cannot be accomplished as a method of organizing human activity, and amount to significantly more than merely gathering, analyzing, and outputting data.

Implementations of the present invention include implementing (executing, running, or deploying) one or more artificial intelligence models on a computing device wherein the computing device executes the artificial intelligence model's algorithms and mathematical functions on computer hardware using machine learning libraries. The computing device implements the artificial intelligence model when it performs tasks like training, making predictions, applying the model to data, decision-making, classification, or generating outputs based on inputs. In particular, the speed at which an artificial intelligence model analyzes and transforms data to effectuate the disclosed method, system, or product would involve large-scale, continuous transformation of such data. As such, the present invention would be impossible to accomplish on pen and paper or in the human mind due to the volume of data being analyzed and transformed by the artificial intelligence model.

FIG. 1 illustrates an example of a computer system 100 that may be utilized to execute various procedures, including the processes described herein. The computer system 100 comprises a standalone computer or mobile computing device, a mainframe computer system, a workstation, a network computer, a desktop computer, a laptop, or the like. The computer system 100 can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive).

In some embodiments, the computer system 100 includes one or more processors 110 coupled to a memory 120 through a system bus 180 that couples various system components, such as an input/output (I/O) devices 130, to the processors 110. The bus 180 may be any of several types of bus structures including a memory bus or memory controller, a peripheral bus, and a local bus using any of a variety of bus architectures. For example, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

In some embodiments, the computer system 100 includes one or more input/output (I/O) devices 130, such as video device(s) (e.g., a camera), audio device(s), and display(s) are in operable communication with the computer system 100. In some embodiments, similar I/O devices 130 may be separate from the computer system 100 and may interact with one or more nodes of the computer system 100 through a wired or wireless connection, such as over a network interface.

Processors 110 suitable for the execution of computer readable program instructions include both general and special purpose microprocessors and any one or more processors of any digital computing device. For example, each processor 110 may be a single processing unit or a number of processing units and may include single or multiple computing units or multiple processing cores. The processor(s) 110 can be implemented as one or more microprocessors, microcomputers, microcontrollers, digital signal processors, central processing units, state machines, logic circuitries, and/or any devices that manipulate signals based on operational instructions. For example, the processor(s) 110 may be one or more hardware processors and/or logic circuits of any suitable type specifically programmed or configured to execute the algorithms and processes described herein. The processor(s) 110 can be configured to fetch and execute computer readable program instructions stored in the computer-readable media, which can program the processor(s) 110 to perform the functions described herein.

In this disclosure, the term "processor" can refer to substantially any computing processing unit or device, including single-core processors, single-processors with software multithreading execution capability, multi-core processors, multi-core processors with software multithreading execution capability, multi-core processors with hardware multithread technology, parallel platforms, and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures, such as molecular and quantum-dot based transistors, switches, and gates, to optimize space usage or enhance performance of user equipment. A processor can also be implemented as a combination of computing processing units.

In some embodiments, the memory 120 includes computer-readable application instructions 140, configured to implement certain embodiments described herein, and a database 150, comprising various data accessible by the application instructions 140. In some embodiments, the application instructions 140 include software elements corresponding to one or more of the various embodiments described herein. For example, application instructions 140 may be implemented in various embodiments using any desired programming language, scripting language, or combination of programming and/or scripting languages (e.g., Android, C, C++, C#, JAVA, JAVASCRIPT, PERL, etc.).

In this disclosure, terms "store," "storage," "data store," data storage," "database," and substantially any other information storage component relevant to operation and functionality of a component are utilized to refer to "memory components," which are entities embodied in a "memory," or components comprising a memory. Those skilled in the art would appreciate that the memory and/or memory components described herein can be volatile memory, nonvolatile memory, or both volatile and nonvolatile memory. Nonvolatile memory can include, for example, read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include, for example, RAM, which can act as external cache memory. The memory and/or memory components of the systems or computer-implemented methods can include the foregoing or other suitable types of memory.

Generally, a computing device will also include or be operatively coupled to receive data from or transfer data to, or both, one or more mass data storage devices; however, a computing device need not have such devices. The computer readable storage medium (or media) can be a tangible device that can retain and store instructions for use by an instruction execution device. The computer readable storage medium can be, for example, an electronic storage device, a magnetic storage device, an optical storage device, an electromagnetic storage device, a semiconductor storage device, or any suitable combination of the foregoing. A non-exhaustive list of more specific examples of the computer readable storage medium can include: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. In this disclosure, a computer readable storage medium is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

In some embodiments, the steps and actions of the application instructions 140 described herein are embodied directly in hardware, in a software module executed by a processor, or in a combination of the two. A software module may reside in RAM, flash memory, ROM memory, EPROM memory, EEPROM memory, registers, a hard disk, a removable disk, a CD-ROM, or any other form of storage medium known in the art. An exemplary storage medium may be coupled to the processor 110 such that the processor 110 can read information from, and write information to, the storage medium. In the alternative, the storage medium may be integrated into the processor 110. Further, in some embodiments, the processor 110 and the storage medium may reside in an Application Specific Integrated Circuit (ASIC). In the alternative, the processor and the storage medium may reside as discrete components in a computing device. Additionally, in some embodiments, the events or actions of a method or algorithm may reside as one or any combination or set of codes and instructions on a machine-readable medium or computer-readable medium, which may be incorporated into a computer program product.

In some embodiments, the application instructions 140 for carrying out operations of the present disclosure can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The application instructions 140 can execute entirely on the user's computer, partly on the user's computer, as a stand-alone software package, partly on the user's computer and partly on a remote computer, or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present disclosure.

In some embodiments, the application instructions 140 can be downloaded to a computing/processing device from a computer readable storage medium, or to an external computer or external storage device via a network 190. A network adapter card or network interface in each computing/processing device receives computer readable program instructions from the network and forwards the computer readable application instructions 140 for storage in a computer readable storage medium within the respective computing/processing device.

In some embodiments, the computer system 100 includes one or more interfaces 160 that allow the computer system 100 to interact with other systems, devices, or computing environments. In some embodiments, the computer system 100 comprises a network interface 165 to communicate with a network 190. In some embodiments, the network interface 165 is configured to allow data to be exchanged between the computer system 100 and other devices attached to the network 190, such as other computer systems, or between nodes of the computer system 100. In various embodiments, the network interface 165 may support communication via wired or wireless general data networks, such as any suitable type of Ethernet network, for example, via telecommunications/telephony networks such as analog voice networks or digital fiber communications networks, via storage area networks such as Fiber Channel SANs, or via any other suitable type of network and/or protocol. Other interfaces include the user interface 170 and the peripheral device interface 175.

In some embodiments, the network 190 corresponds to a local area network (LAN), wide area network (WAN), the Internet, a direct peer-to-peer network (e.g., device to device Wi-Fi, Bluetooth, etc.), and/or an indirect peer-to-peer network (e.g., devices communicating through a server, router, or other network device). The network 190 can comprise copper transmission cables, optical transmission fibers, wireless transmission, routers, firewalls, switches, gateway computers and/or edge servers. The network 190 can represent a single network or multiple networks. In some embodiments, the network 190 used by the various devices of the computer system 100 is selected based on the proximity of the devices to one another or some other factor. For example, when a first user device and second user device are near each other (e.g., within a threshold distance, within direct communication range, etc.), the first user device may exchange data using a direct peer-to-peer network. But when the first user device and the second user device are not near each other, the first user device and the second user device may exchange data using a peer-to-peer network (e.g., the Internet). The Internet refers to the specific collection of networks and routers communicating using an Internet Protocol ("IP") including higher level protocols, such as Transmission Control Protocol/Internet Protocol ("TCP/IP") or the Uniform Datagram Packet/Internet Protocol ("UDP/IP").

Any connection between the components of the system may be associated with a computer-readable medium. For example, if software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. As used herein, the terms "disk" and "disc" include compact disc (CD), laser disc, optical disc, digital versatile disc (DVD), floppy disk, and Blu-ray disc; in which "disks" usually reproduce data magnetically, and "discs" usually reproduce data optically with lasers. Combinations of the above should also be included within the scope of computer-readable media. In some embodiments, the computer-readable media includes volatile and nonvolatile memory and/or removable and non-removable media implemented in any type of technology for storage of information, such as computer-readable instructions, data structures, program modules, or other data. Such computer-readable media may include RAM, ROM, EEPROM, flash memory or other memory technology, optical storage, solid state storage, magnetic tape, magnetic disk storage, RAID storage systems, storage arrays, network attached storage, storage area networks, cloud storage, or any other medium that can be used to store the desired information and that can be accessed by a computing device. Depending on the configuration of the computing device, the computer-readable media may be a type of computer-readable storage media and/or a tangible non-transitory media to the extent that when mentioned, non-transitory computer-readable media exclude media such as energy, carrier signals, electromagnetic waves, and signals per se.

In some embodiments, the system is world-wide-web (www) based, and the network server is a web server delivering HTML, XML, etc., web pages to the computing devices. In other embodiments, a client-server architecture may be implemented, in which a network server executes enterprise and custom software, exchanging data with custom client applications running on the computing device.

In some embodiments, the system can also be implemented in cloud computing environments. In this context, "cloud computing" refers to a model for enabling ubiquitous, convenient, on-demand network access to a shared pool of configurable computing resources (e.g., networks, servers, storage, applications, and services) that can be rapidly provisioned via virtualization and released with minimal management effort or service provider interaction, and then scaled accordingly. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

As used herein, the term "add-on" (or "plug-in") refers to computing instructions configured to extend the functionality of a computer program, where the add-on is developed specifically for the computer program. The term "add-on data" refers to data included with, generated by, or organized by an add-on. Computer programs can include computing instructions, or an application programming interface (API) configured for communication between the computer program and an add-on. For example, a computer program can be configured to look in a specific directory for add-ons developed for the specific computer program. To add an add-on to a computer program, for example, a user can download the add-on from a website and install the add-on in an appropriate directory on the user's computer.

In some embodiments, the computer system 100 may include a user computing device 145, an administrator computing device 185 and a third-party computing device 195 each in communication via the network 190. The user computing device 145 may be utilized by a user to interact with the various functionalities of the system. The administrator computing device 185 is utilized by an administrative user to moderate content and to perform other administrative functions. The third-party computing device 195 may be utilized by third parties to receive communications from the user computing device, transmit communications to the user via the network, and otherwise interact with the various functionalities of the system.

Figure 2:
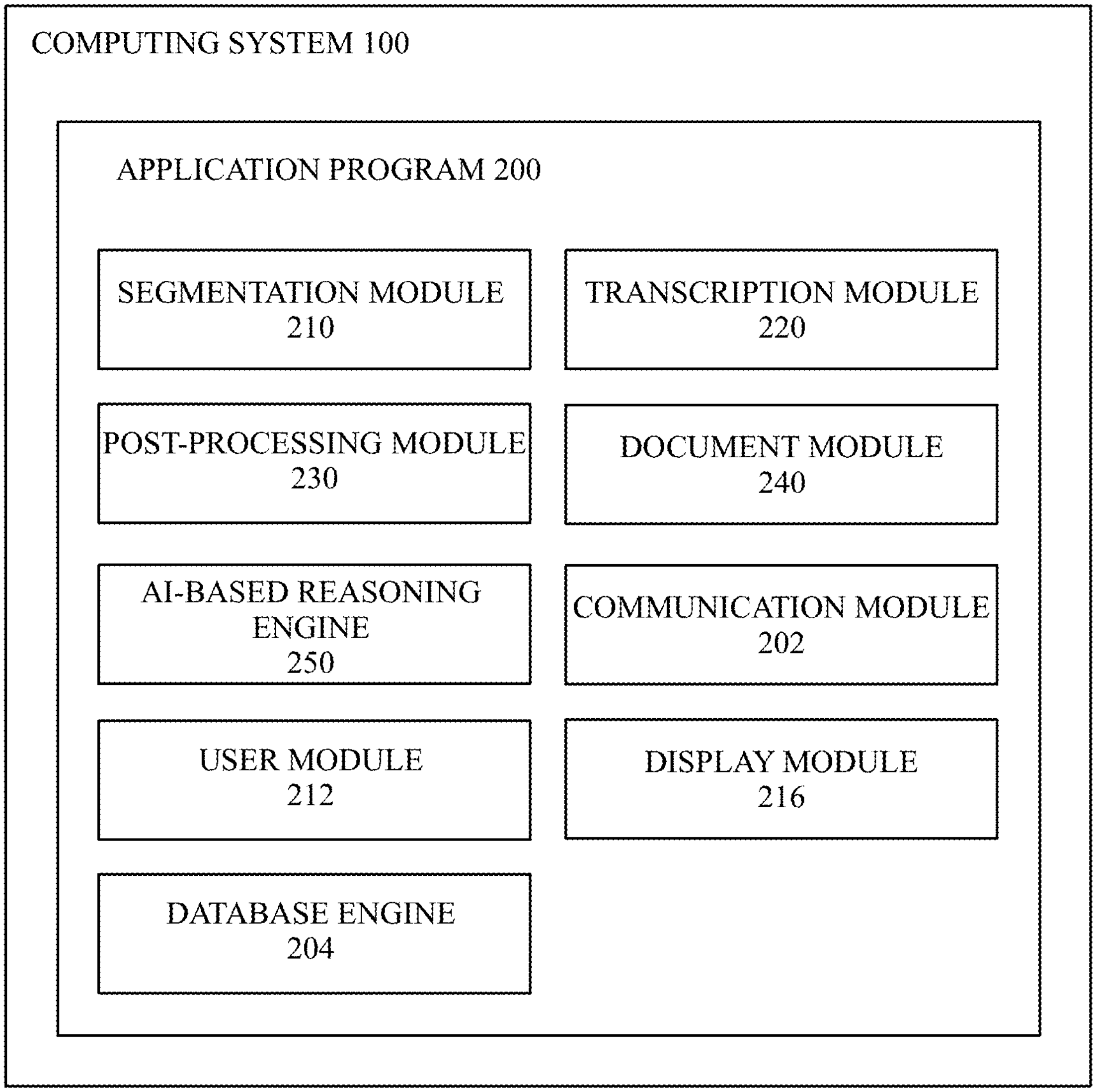
FIG. 2 illustrates an application program and modules in communication with the computing system, according to some embodiments.

FIG. 2 illustrates an example computer architecture for the application program 200 operated via the computing system 100. In some embodiments, the computing system 100 functions as an intermediate computing device including a microphone configured to record and communicate real-time audio to a local, on-premises, private, or cloud-based server or processor. In some embodiments, the computing system 100 functions as the local, on-premises, private, or cloud-based server or processor configured to receive recorded audio from a wearable device including a microphone. The computer system 100 comprises several modules and engines configured to execute the functionalities of the application program 200, and a database engine 204 configured to facilitate how data is stored and managed in one or more databases. In particular, FIG. 2 is a block diagram showing the modules and engines needed to perform specific tasks within the application program 200.

Referring to FIG. 2, the computing system 100 operating the application program 200 comprises one or more modules having the necessary routines and data structures for performing specific tasks, and one or more engines configured to determine how the platform manages and manipulates data. In some embodiments, the application program 200 comprises one or more of a segmentation module 210, a transcription module 220, a post-processing module 230, a document module 240, an AI-based reasoning engine 250, a communication module 202, a database engine 204, a user module 212, and a display module 216.

In some embodiments, the AI-based reasoning engine 250 is configured to coordinate managing data flow between the segmentation module 210, transcription module 220, post-processing module 230, and document module 240. The AI-based reasoning engine 250 optimizes real-time processing, decision-making, and adaptation of audio processing, segmentation, transcription, post-processing, and structured documentation rules between each of the segmentation module 210, transcription module 220, post-processing module 230, and document module 240. In embodiments, the AI-based reasoning engine 250 is configured to operate as a model hub between the AI or ML models of the segmentation module 210, transcription module 220, post-processing module 230, and document module 240, where pre-trained artificial intelligence and machine learning models are stored, shared, and accessed.

In some embodiments, the segmentation module 210 is configured to receive audio from a wearable computing device (e.g., a headset, lapel microphone, or other sterile-compatible audio input device) capable of real-time audio recording. The module may employ a convolutional neural network for feature extraction and long short-term memory networks (CNN-LSTM) for sequence modeling, procedural context analysis, and acoustic analysis to divide the real-time narration into discrete segments. In embodiments, the segmentation module 210 is configured to employ a custom speech detection model that identifies segments in audio recordings where speech is present. The segmentation module 210 filters out durations of silence where necessary. The segmentation module 210 then passes audio segments to a segment classifier that determines if the detected speech segment is a background conversation, noise, ongoing conversation between the active surgeon and colleagues, or narration for an automated note. The segmentation module 210 then returns the speech segments that are most relevant to the procedure notes. This segmentation ensures that each part of the transcript corresponds to distinct phases of the procedure, such as preoperative preparation, incision, closure, or postoperative care, for example.

In some embodiments, the transcription module 220 is configured to process segmented audio using a parallel transcription pipeline with multiple speech-to-text models. These models include deep learning-based speech recognition models, such as transformer-based ASR models, that analyze the segmented audio. The transcription module 220 is configured to identify phonemes, multiple languages, dialects, linguistic structures, and procedural terminology, ensuring high accuracy. In some embodiments, the transcription module 220 is configured to process audio data in an input language or dialect and output text transcription in a different, user-preferred language using computer-based translation. The transcription module 220 is pre-trained on extensive medical datasets to recognize surgical terminology, abbreviations, and procedural steps.

In some embodiments, the post-processing module 230 is configured to refine the transcription generated via the transcription module 220 by applying heuristic-based filtering (for example, to fix common spelling errors, punctuation issues, missing section titles, identify speech commands), contextual reorganization, and medical domain-specific corrections. The post-processing module 230 incorporates semantic analysis to detect primary procedural components, syntactic alignment models to ensure proper sentence structure, and noise filtering algorithms to remove irrelevant audio artifacts. Additionally, an auto-correction system cross-references detected terms against a medical knowledge base to validate terminology and ensure coherence.

In some embodiments, the document module 240 is configured to receive the processed transcript and organize the information into a structured format aligned with standard surgical documentation protocols using a large language model (LLM) configured to ingest raw or processed narration transcript and return structured and organized post-operative notes based on the LLM's pre-training, fine-tuning, and prompting based on standard or institutional templates. The structured notes may be generated in formats such as SOAP (Subjective, Objective, Assessment, Plan) notes, SNOMED CT (Systematized Nomenclature of Medicine-Clinical Terms), or custom institutional templates. In some embodiments, the system allows customization based on hospital-specific procedural note requirements, enabling automated compliance with regulatory standards. In some embodiments, the document module 240 is configured to identify and retrieve relevant billing codes such as ICD and SNOMED codes; drug codes for anesthetic agent use; or important clinical concepts or events that may be actionable post-operatively. For example, if post-op blood work audio was recorded, the document module 240 prompts the surgeon to order the labs or drugs by including notes within the transcript to do so. In embodiments, the document module 240 is configured to provide suggestions for follow up care and post-operative management based on evidence-based treatment protocols and guidelines, such as the previously mentioned lab or drug orders.

In some embodiments, the communication module 202 is configured for receiving, processing, and transmitting a user command and/or one or more data streams. In such embodiments, the communication module 202 performs communication functions between various devices, including the user computing device 145 of FIG. 1, the administrator computing device 185 of FIG. 1, and a third-party computing device 195 of FIG. 1. In some embodiments, the communication module 202 is configured to allow one or more users of the system, including a third-party, to communicate with one another. In some embodiments, the communications module 202 is configured to maintain one or more communication sessions with one or more servers, the administrative computing device 185 of FIG. 1, and/or one or more third-party computing device(s) 195 of FIG. 1. In some embodiments, the communication module 202 may allow users and administrators to communicate with one another.

In some embodiments, a database engine 204 is configured to facilitate the storage, management, and retrieval of data to and from one or more storage mediums, such as the one or more internal databases described herein. It stores the incoming audio stream, the audio segments, the raw and intermediate versions of transcripts as well as the finalized procedure or post-operative note. In some embodiments, the database engine 204 is coupled to an external storage system. In some embodiments, the database engine 204 is configured to apply changes to one or more databases. In some embodiments, the database engine 204 comprises a search engine component for searching through thousands of data sources stored in different locations. In some embodiments, the data storage module serves as a temporary store for the original audio narration in the event that quality control (QC) is required for the automated document generation process.

The user module 212 may store user preferences including the user account information, historical usage data, user personal information, and the like. The user module 212 may facilitate the creation of user's profiles for users, administrators, and others.

In some embodiments, the display module 216 is configured to display one or more graphic user interfaces, including, e.g., one or more user interfaces. In some embodiments, the display module 216 is configured to temporarily generate and display various pieces of information in response to one or more commands or operations. The various pieces of information or data generated and displayed may be transiently generated and displayed, and the displayed content in the display module 216 may be refreshed and replaced with different content upon the receipt of different commands or operations in some embodiments. In such embodiments, the various pieces of information generated and displayed in a display module 216 may not be persistently stored. The display module 216 displays information, notifications, and alerts to the user device which can be viewed and acknowledged by the user.

Figure 3:
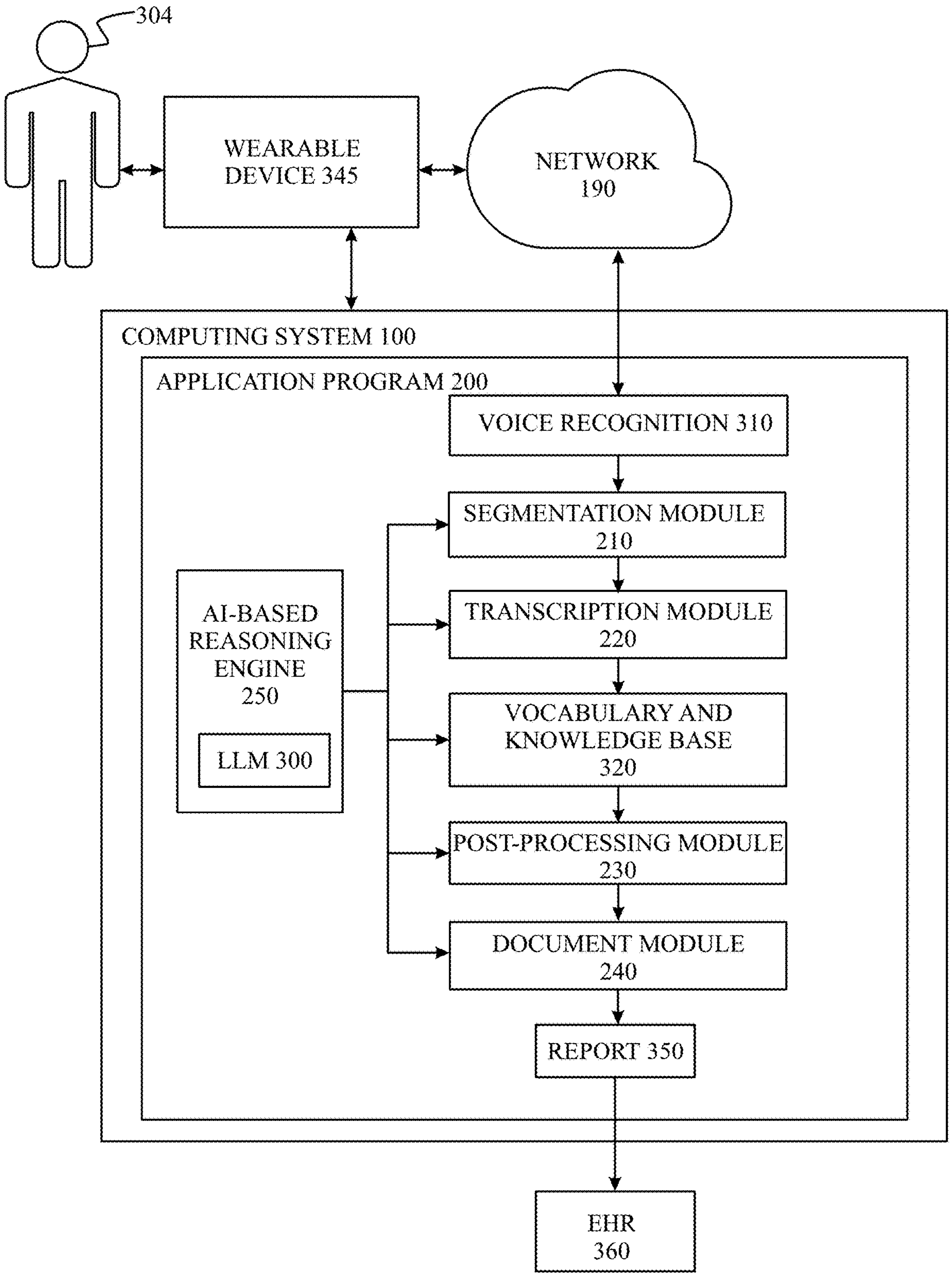
FIG. 3 illustrates a block diagram of a system to generate structured surgical operation and procedure notes using voice narration during surgery, according to some embodiments.

FIG. 3 illustrates a block diagram of a system to generate structured surgical or medical operation and procedure notes using voice narration during surgery, wherein a user 304, such a surgeon, wearing or using a wearable device 345 including a microphone is in operable communication with a network 190 or computing system 100 as previously described. The computing system 100 may be configured to execute the application program 200 of FIG. 2, including each of the segmentation module 210, a transcription module 220, a post-processing module 230, a document module 240, an AI-based reasoning engine 250, a communication module 202, a database engine 204, a user module 212, and a display module 216. The application program 200 is configured to, via the AI-based reasoning engine 250, which may use the segmentation module 210 to identify speech within audio recorded via the wearable device 345 via voice recognition 310. Recorded audio may be segmented via the segmentation module 210, wherein segmented audio chunks may be processed in parallel. Audio chunks may be transcribed in parallel via the transcription module 220 using two or more instances of voice-to-text or speech recognition models. The transcription module 220 may combine transcribed sections into a single transcript and generate, using heuristics or LLM 300, structured operation notes based on the single transcript or sections. A post-processing module 230 may alter the single transcript, or transcribed sections into the structured operation notes using heuristics or the LLM 300. A report 350 may then be generated via the document module 240 containing the transcript, and the transcript may be transmitted to an EHR 360.

Figure 4:
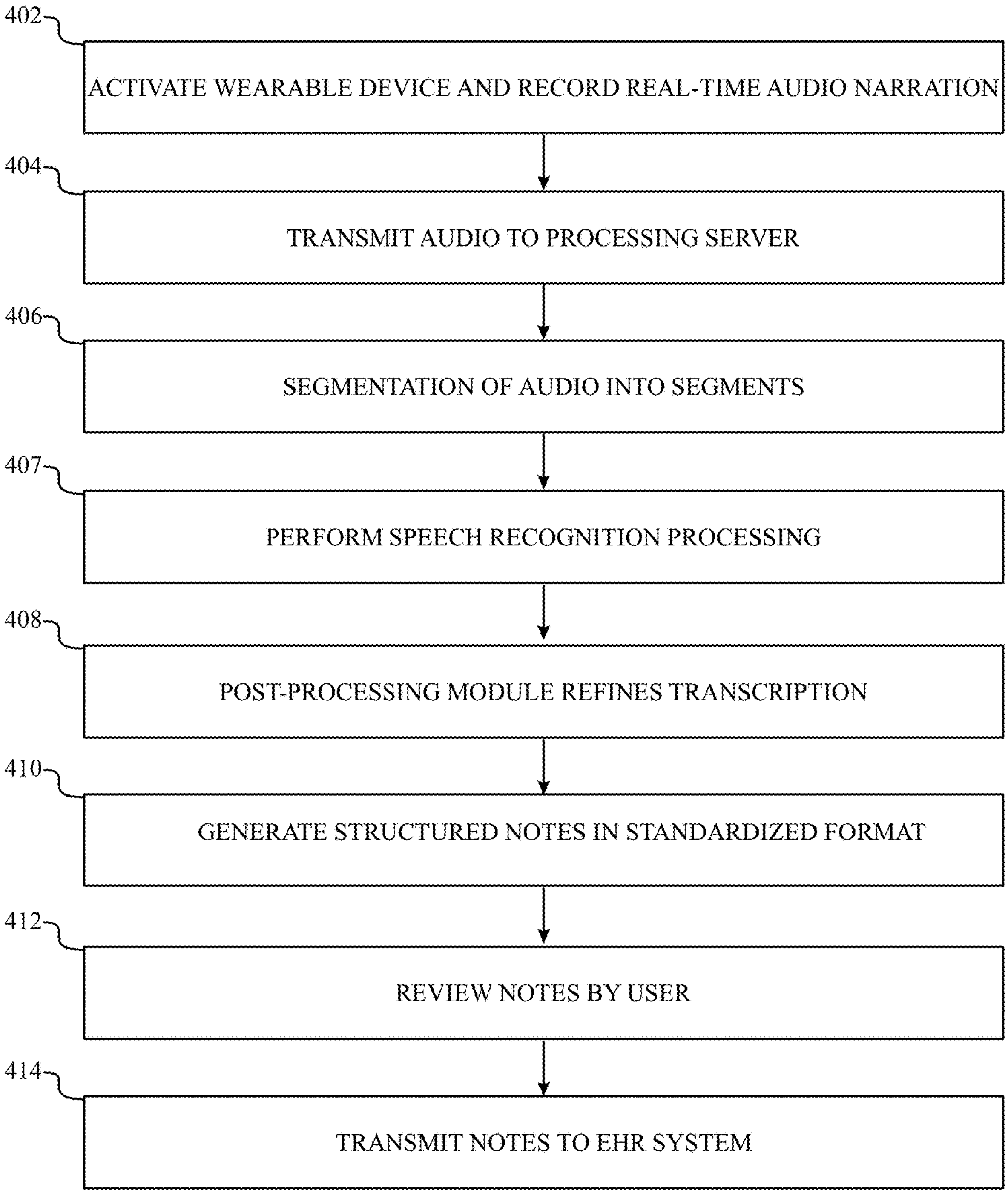
FIG. 4 illustrates a flowchart of generating structured surgical operation and procedure notes using voice narration during surgery, according to some embodiments.

FIG. 4 illustrates a flowchart of generating structured surgical or medical operation and procedure notes using real-time voice narration during surgery. The method may include, in step 402, a surgeon activates a wearable device and records real-time audio narration of a medical procedure. In step 404, the method may include transmitting the recorded audio to a processing server. In step 406, the system may segment recorded audio into segments via the segmentation module. In step 407, the system performs speech recognition processing of the segmented audio, such as via transformer-based ASR models. In step 408, the system may process segmented audio in parallel and transcribe audio into text using noise filtering, medical terminology correction, accent-aware transcription, etcetera. In step 410, the system may reformat transcribed notes into standardized formats. In step 412, the system may display standardized notes on a user interface for a user to review and edit as needed. In step 414, the system may transmit transcribed notes to an EHR system.

Figure 5:
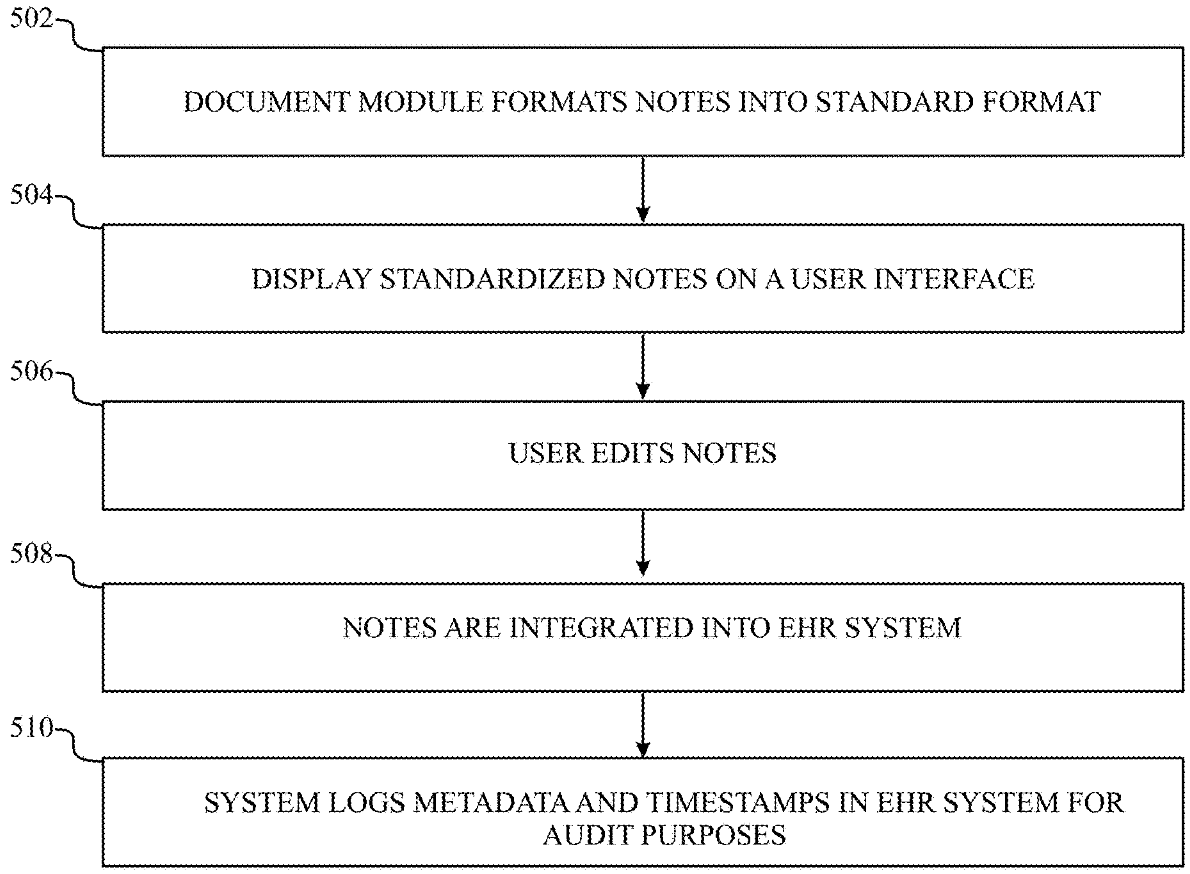
FIG. 5 illustrates a flowchart of generating structured surgical operation and procedure notes using voice narration during surgery, according to some embodiments.

FIG. 5 illustrates a flowchart of generating structured surgical or medical operation and procedure notes using voice narration during surgery including a structured documentation generation and review process. In step 502, the system may format transcribed audio notes into a standard format via the document module. In step 504, the system may display the standardized notes on a user interface of a device. In step 506, a user may edit the notes. In step 508, the system may transmit the notes to an EHR or HIS system. In step 510, the system logs metadata (including edits made to the generated note) and timestamps associated with the recorded audio and transcribed notes for audit purposes.

Figure 6:
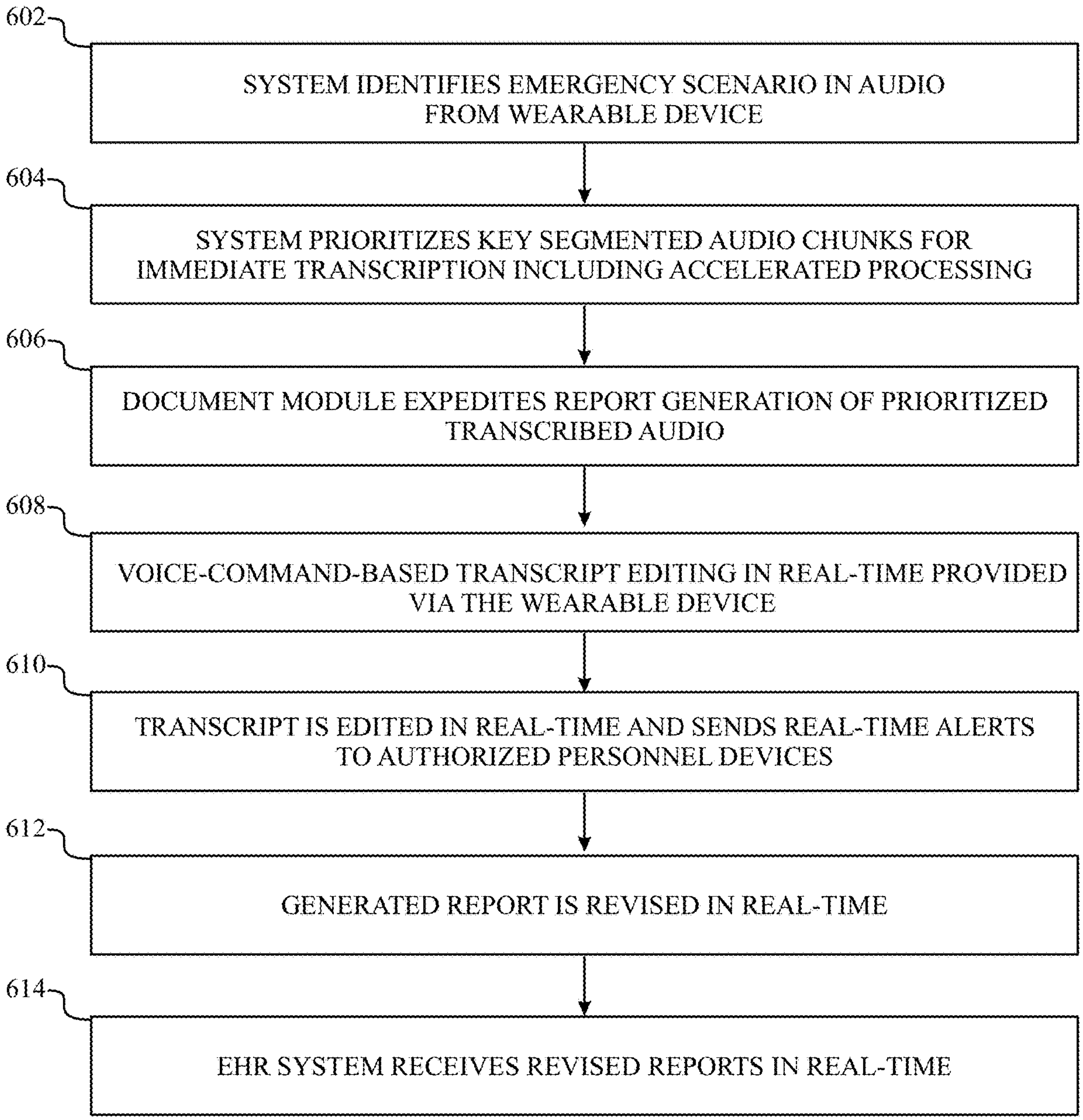
FIG. 6 illustrates a flowchart of generating structured surgical operation and procedure notes using voice narration during surgery, according to some embodiments.

FIG. 6 illustrates a flowchart of generating structured surgical or medical operation and procedure notes using voice narration during surgery including an emergency mode workflow for critical situations. In step 602, the system detects an emergency scenario within record audio (e.g., emergency room, trauma surgery, critical intervention) by detecting audio indicative of an emergency scenario using speech recognition. In step 604, the system prioritizes key procedural sections of recorded audio for immediate transcription including accelerating low-latency processing of essential information. In step 606, the system expedites report generation of prioritized transcribed audio. In step 608, the system allows for voice-command-based editing for hands-free modification of transcribed audio. In step 610, the system edits transcriptions in real time and sends real-time alerts to authorized personnel devices. In step 612, the system generates or revises a report in real-time based on emergency audio or user real-time voice-command-based editing. In step 614, the system updates an EHR or HIS system with revised reports in real-time.

In this disclosure, the various embodiments are described with reference to the flowchart illustrations and/or block diagrams of methods, apparatus (systems), and computer program products. Those skilled in the art would understand that each block of the flowchart illustrations and/or block diagrams, and combinations of blocks in the flowchart illustrations and/or block diagrams, can be implemented by computer readable program instructions. The computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions or acts specified in the flowchart and/or block diagram block or blocks. The computer readable program instructions can be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can be loaded onto a computer, other programmable data processing apparatus, or other device to cause a series of operational acts to be performed on the computer, other programmable apparatus, or other device to produce a computer implemented process, such that the instructions that execute on the computer, other programmable apparatus, or other device implement the functions or acts specified in the flowchart and/or block diagram block or blocks.

In this disclosure, the block diagrams in the Figures illustrate the architecture, functionality, and operation of possible implementations of systems, methods, and computer program products according to the various embodiments. Each block in the flowchart or block diagrams can represent a module, segment, or portion of instructions, which comprises one or more executable instructions for implementing the specified logical function(s). In some embodiments, the functions noted in the blocks can occur out of the order noted in the Figures. For example, two blocks shown in succession can, in fact, be executed concurrently or substantially concurrently, or the blocks can sometimes be executed in the reverse order, depending upon the functionality involved. In some embodiments, each block of the block diagrams and/or flowchart illustration, and combinations of blocks in the block diagrams and/or flowchart illustration, can be implemented by a special purpose hardware-based system that performs the specified functions or acts or carry out combinations of special purpose hardware and computer instructions.

In this disclosure, the subject matter has been described in the general context of computer-executable instructions of a computer program product running on a computer or computers, and those skilled in the art would recognize that this disclosure can be implemented in combination with other program modules. Generally, program modules include routines, programs, components, data structures, etc. that perform particular tasks and/or implement particular abstract data types. Those skilled in the art would appreciate that the computer-implemented methods disclosed herein can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated embodiments can be practiced in distributed computing environments where tasks are performed by remote processing devices that are linked through a communications network. Some embodiments of this disclosure can be practiced on a stand-alone computer. In a distributed computing environment, program modules can be located in both local and remote memory storage devices.

In this disclosure, the terms "component," "system," "platform," "interface," and the like, can refer to and/or include a computer-related entity or an entity related to an operational machine with one or more specific functionalities. The disclosed entities can be hardware, a combination of hardware and software, software, or software in execution. For example, a component can be a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As another example, a component can be an apparatus that provides specific functionality through electronic components without mechanical parts, wherein the electronic components can include a processor or other means to execute software or firmware that confers at least in part the functionality of the electronic components. In some embodiments, a component can emulate an electronic component via a virtual machine, e.g., within a cloud computing system.

The phrase "application" as is used herein means software other than the operating system, such as Word processors, database managers, Internet browsers and the like. Each application generally has its own user interface, which allows a user to interact with a particular program. The user interface for most operating systems and applications is a graphical user interface (GUI), which uses graphical screen elements, such as windows (which are used to separate the screen into distinct work areas), icons (which are small images that represent computer resources, such as files), pull-down menus (which give a user a list of options), scroll bars (which allow a user to move up and down a window) and buttons (which can be "pushed" with a click of a mouse). A wide variety of applications is known to those in the art.

The phrases "Application Program Interface" and API as are used herein mean a set of commands, functions and/or protocols that computer programmers can use when building software for a specific operating system. The API allows programmers to use predefined functions to interact with an operating system, instead of writing them from scratch. Common computer operating systems, including Windows, Unix, and the Mac OS, usually provide an API for programmers. An API is also used by hardware devices that run software programs. The API generally makes a programmer's job easier, and it also benefits the end user since it generally ensures that all programs using the same API will have a similar user interface.

The phrases "computing device" or "central processing unit" as is used herein means a computer hardware component that executes individual commands of a computer software program. It reads program instructions from a main or secondary memory, and then executes the instructions one at a time until the program ends. During execution, the program may display information to an output device such as a monitor.

The term "execute" as is used herein in connection with a computer, console, server system or the like means to run, use, operate or carry out an instruction, code, software, program and/or the like.

In this disclosure, the descriptions of the various embodiments have been presented for purposes of illustration and are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein. Thus, the appended claims should be construed broadly, to include other variants and embodiments, which may be made by those skilled in the art.

It will be appreciated by persons skilled in the art that the present embodiment is not limited to what has been particularly shown and described hereinabove. A variety of modifications and variations are possible considering the above teachings without departing from the following claims.

What is claimed is:

1. A computer-implemented method for generating structured surgical or medical operation and procedure notes using voice narration during surgery, the method comprising:

recording, via a wearable computing device comprising at least one microphone, real-time audio;

communicating, via the wearable computing device or intermediate computing device, the real-time audio to a local, on-premises, private, or cloud-based server or processor;

sectioning intelligently, via the processor or server, the real-time audio, including: identifying, via a speech detection model, one or more segments of the real-time audio in which speech is present; classifying, via a segment classifier, each of the one or more segments as one of a background conversation, noise, an ongoing conversation between an active surgeon and one or more colleagues, or a narration for an automated note; and returning, as most relevant to the structured operation notes, the one or more segments classified as the narration for the automated note;

transcribing, via the processor or server, the sectioned real-time audio data in parallel via two or more instances of voice-to-text or speech recognition models;

combining, via the processor or server, transcribed sections into a single transcript;

generating, via a post-processing step, heuristics, or large language model, structured operation notes based on the single transcript or sections; and altering, via post-processing steps, heuristics, or the large language model, the single transcript, or transcribed sections into the structured operation notes.

2. The computer-implemented method of claim 1, wherein the sectioning comprises intelligently separating the real-time audio into portions of audio data based on real-time recording voice data relevant to the procedure and within the recorded real-time audio.

3. The computer-implemented method of claim 1, wherein the sectioning occurs based on natural language processing of spoken utterances or dialogue within the structured operation notes.

4. The computer-implemented method of claim 1, further comprising instructing at least one of an augmented reality or virtual reality device to display the single transcript.

5. The computer-implemented method of claim 1, wherein the transcribing comprises utilizing a speech recognition model to analyze an audio waveform, identifying phonemes within the audio waveform, and reconstructing the phonemes into words based on linguistic patterns within the audio waveform.

6. The computer-implemented method of claim 1, wherein the combining comprises postprocessing, heuristics, or LLM-based refinement of the transcription.

7. The computer-implemented method of claim 1, wherein the generated structured operation note utilizes one or more linguistic patterns, semantic analysis, or attention mechanisms to identify primary ideas within the single narration transcript, wherein the primary ideas correlate to the structured operation notes.

8. The computer-implemented method of claim 1, wherein the altering comprises contextually reorganizing the single transcript into the structured operation notes based on the contextual reorganization.

9. A system comprising:

at least one computing device in operable communication with a network configured to host an application program configured to:

record by itself natively, or via a wearable computing device comprising at least one microphone, real-time audio;

an application server in operable communication with the at least one computing device over the network, the application server configured to host the application program configured to:

record, via a wearable computing device comprising at least one microphone, real-time audio;

communicate, via the wearable computing device, the real-time audio to a local, on premises, private, or cloud-based server;

section the real-time audio to remove irrelevant audio sections, including: identifying, via a speech detection model, one or more segments of the real-time audio in which speech is present; classifying, via a segment classifier, each of the one or more segments as one of a background conversation, noise, an ongoing conversation between an active surgeon and one or more colleagues, or a narration for an automated note; and returning, as most relevant to the structured operation notes, the one or more segments classified as the narration for the automated note;

transcribe sectioned real-time audio data in parallel via two or more instances of a voice-to-text or speech recognition models;

combine transcribed sections into a single transcript;

generate, via a large language model, heuristics, or post-processing, structured operation notes based on the single transcript; and alter, via the large language model, the single transcript to include the structured operation notes.

10. The system of claim 9, wherein the sectioning comprises separating audio into portions of relevant audio data based on recording voice data within the recorded audio.

11. The system of claim 9, wherein the sectioning occurs based on feature extraction performed by a convolutional neural network and sequence modeling performed by a long short-term memory network (CNN-LSTM) modeling of spoken speech, narration, or dialogue within the audio.

12. The system of claim 9, wherein the application program is further configured to: instruct at least one of an augmented reality or virtual reality device to display the single transcript.

13. The system of claim 9, wherein the transcribing comprises utilizing a speech recognition model to analyze an audio waveform, identifying phonemes within the audio waveform, and reconstructing the phonemes into words based on linguistic patterns within the audio waveform.

14. The system of claim 9, wherein the combining comprises heuristics, post-processing, or LLM-based transcription.

15. The system of claim 9, wherein the generating structured operation notes utilizes one or more linguistic patterns, semantic analysis, or attention mechanisms to identify primary ideas within the single transcript, wherein the primary ideas correlate to the structured operation notes.

16. The system of claim 9, wherein the altering comprises:

contextually reorganizing the single transcript into the structured operation notes; and integrating the structured operation notes into the single transcript based on the contextual reorganization.

17. A software product comprising at least one non-transitory computer readable storage media having application instructions collectively stored on the at least one non-transitory computer readable storage media, the application instructions executable to:

record, via a wearable computing device comprising at least one microphone, real-time audio;

communicate, via the wearable computing device, the real-time audio to a local, on-premises, private, or cloud-based server;

section the real-time audio, including: identifying, via a speech detection model, one or more segments of the real-time audio in which speech is present; classifying, via a segment classifier, each of the one or more segments as one of a background conversation, noise, an ongoing conversation between an active surgeon and one or more colleagues, or a narration for an automated note; and returning, as most relevant to the structured operation notes, the one or more segments classified as the narration for the automated note;

transcribe sectioned real-time audio data in parallel via two or more voice-to-text or speech recognition models;

combine transcribed sections into a single transcript;

generate, via a large language model, heuristics, or post-processing, structured operation notes based on the single transcript; and alter, via the large language model, the single transcript to include the structured operation notes.

* * * * *